United States Patent [19]

Durham et al.

[11] Patent Number: 5,679,957
[45] Date of Patent: Oct. 21, 1997

[54] METHOD AND APPARATUS FOR MONITORING MERCURY EMISSIONS

[75] Inventors: Michael D. Durham, Castle Rock; Richard J. Schlager, Aurora; Andrew D. Sappey, Golden; Francis J. Sagan, Lakewood; Roger W. Marmaro; Kevin G. Wilson, both of Littleton, all of Colo.

[73] Assignee: ADA Technologies, Inc., Englewood, Colo.

[21] Appl. No.: 583,163

[22] Filed: Jan. 4, 1996

[51] Int. Cl.$^6$ ................................................ G01N 21/59
[52] U.S. Cl. ............................................................. 250/373
[58] Field of Search .................................................. 250/373

[56] References Cited

U.S. PATENT DOCUMENTS

| | | |
|---|---|---|
| 3,173,016 | 3/1965 | Williston . |
| 3,178,572 | 4/1965 | Williston . |
| 3,281,596 | 10/1966 | Williston . |
| 3,449,565 | 6/1969 | Barringer . |
| 3,544,789 | 12/1970 | Wieder . |
| 3,676,004 | 7/1972 | Prugger et al. . |
| 3,704,097 | 11/1972 | Capuano . |
| 3,711,248 | 1/1973 | Coffey . |
| 3,778,162 | 12/1973 | Gant et al. . |
| 3,844,719 | 10/1974 | Hammitt . |
| 3,852,604 | 12/1974 | Grengg . |
| 3,884,639 | 5/1975 | Sugiyama . |
| 3,888,124 | 6/1975 | Campbell et al. . |
| 3,914,054 | 10/1975 | Hadeishi . |
| 3,933,431 | 1/1976 | Trujillo et al. . |
| 3,940,614 | 2/1976 | Rhodes et al. . |
| 4,023,929 | 5/1977 | Becker et al. . |
| 4,069,420 | 1/1978 | Ross . |
| 4,138,215 | 2/1979 | Huber . |
| 4,411,867 | 10/1983 | Ostrander ........................ 422/91 |
| 4,441,815 | 4/1984 | Izumi . |
| 4,534,940 | 8/1985 | Bourcier . |
| 4,713,547 | 12/1987 | Grossman . |
| 4,758,519 | 7/1988 | Nakao et al. . |
| 4,853,543 | 8/1989 | Ozdemir . |
| 5,026,652 | 6/1991 | Huber . |
| 5,045,476 | 9/1991 | Huber . |
| 5,068,533 | 11/1991 | Grossman et al. . |
| 5,098,658 | 3/1992 | Huber . |
| 5,314,664 | 5/1994 | Sperling et al. . |

FOREIGN PATENT DOCUMENTS 0368358  8/1994  European Pat. Off. ............. 250/373

OTHER PUBLICATIONS

J. W. Robinson, P. J. Slevin, G. D. Hindman and D. K. Wolcott, "Non–Flame Atomic Absorption in the Vacuum Ultraviolet Region: The Direct Determination of Mercury in Air at the 184.9-nm Resonance Line." *Anal. Chim. Acta* 61 (1972).

Schlager, et al., "Real-Time Analysis Of Total, Elemental And Total Speciated Mercury", Tenth Annual Coal Preparation, Utilization and Environmental Control Contractors Conference, Pittsburgh PA, Jul. 18–21,1994.

Model 791 Continuous Mercury Vapor Monitor.EMP Environmental Inc. Mt. Prospect IL.

HM–1400 Total Mercury Analyzer. Verewa Meβ–und Regettechnik GmbH, Germany.

*Primary Examiner*—Constantine Hannaher
*Attorney, Agent, or Firm*—Sheridan Ross P.C.

[57] ABSTRACT

A mercury monitoring device that continuously monitors the total mercury concentration in a gas. The device uses the same chamber for converting speciated mercury into elemental mercury and for measurement of the mercury in the chamber by radiation absorption techniques. The interior of the chamber is resistant to the absorption of speciated and elemental mercury at the operating temperature of the chamber.

47 Claims, 11 Drawing Sheets

Response of the analyzer to 4.2 μg/m³ of mercury.

Mercury detector response when measuring mercury in the presence of sulfur dioxide.

Linearity of the mercury detector.

Mercuric chloride being converted to elemental mercury.

Dimethyl mercury being converted to elemental mercury.

Monitoring mercury levels at the inlet and outlet of a scrubbing system.

Monitoring mercury levels at the outlet of a scrubber.

METHOD AND APPARATUS FOR MONITORING MERCURY EMISSIONS

This invention was made with Government support under Grant DE-FG02-93ER81501 awarded by the Department of Energy. The Government has certain rights in this invention.

FIELD OF THE INVENTION

The present invention generally relates to the monitoring of mercury in a gas stream and more specifically to the continuous monitoring of speciated and/or elemental mercury in a gas stream.

BACKGROUND OF THE INVENTION

Emissions of elemental mercury (e.g., nonspeciated mercury) and many mercury-containing compounds (e.g., speciated mercury) are strictly regulated in many countries because of significant environmental hazards. Major sources of mercury emissions are waste gases from fossil fuel combustion facilities and municipal solid waste incinerators.

Atomic absorption of ultraviolet radiation is a common method of monitoring mercury levels in waste gases to insure compliance with existing environmental regulations. This technique, however, is only capable of detecting elemental mercury. It is incapable of detecting speciated mercury, which is often a contaminant in industrial waste gases. Unlike elemental mercury, speciated mercury absorbs radiation at a broad range of wavelengths and is therefore, indistinguishable from other nonmercury compounds in the gases. Speciated mercury also does not absorb radiation having a wavelength of 2537 angstroms, which is the primary wavelength at which elemental mercury absorbs radiation.

Before the total mercury concentration in waste gases can be effectively measured by atomic absorption techniques, the speciated mercury is first converted into elemental mercury. After conversion of speciated into elemental mercury but before mercury measurement, the gas is cooled to condense and remove water vapor and the cooled gas is introduced into an atomic absorption instrument for elemental mercury detection and/or measurement.

Four methods are commonly employed to convert speciated into elemental mercury for mercury detection by ultraviolet radiation absorption techniques. In one method, the waste gas is contacted with a noble metal, such as gold or silver, to form an amalgam containing elemental mercury. After removal of the waste gas, the noble metal is heated to above 350° C. to release the elemental mercury as a vapor. This method is a batch sampling technique and therefore is unable to provide real-time mercury measurements for emissions control. The method can yield inaccurate measurements, especially at the low mercury (e.g., 1 ppb) concentrations common in most waste gases. Such inaccuracy can result from the failure of speciated and/or elemental mercury in the waste gas to contact the noble metal. In another method, the gas is heated to a temperature in excess of 900° C. in the presence of a reducing agent to break the molecular bonds between the mercury atoms and the other elements in the speciated mercury. A reducing agent is any substance that will form a compound with the released nonmercury elements to prevent them from recombining with the elemental mercury. The reducing agent can be a liquid, such as stannous chloride, or sulfuric acid, or solid, such as activated carbon in the presence of hydrogen chloride. Typical reducing agents are metals from Groups I (e.g., copper, silver, and gold), II (e.g., zinc and cadmium) and IV (e.g., lead and tin) of the Periodic Table of Elements. At temperatures above 900° C., noble metals such as gold and silver will not form amalgams with mercury but act as reducing agents. The use of a reducing agent to remove elements that can combine with elemental mercury to form speciated mercury is especially important when the gas is cooled to condense and remove water vapor before mercury measurement. In yet another method, a solid is used to absorb the mercury in a gas sample, the solid is decomposed chemically to release the mercury as a vapor, and the mercury vapor is measured. The mercury emission is calculated from the amount of mercury vapor, with the gas sample volume being known. Iodized activated carbon is particularly suitable for use as the solid. Finally, in the last method, the speciated mercury is thermally decomposed at high temperatures of around 800° C. A reverse reaction of the elemental mercury with hydrogen chloride in the waste gas to form speciated mercury must be excluded by first removing the mercury chloride from the waste gas. The hydrogen chloride is removed by an adsorption reaction with lime or silica gel before thermal decomposition.

All of the methods for converting speciated into elemental mercury require periodic maintenance and/or replacement of components to provide as reliable mercury measurements as possible. For example, in the absence of such maintenance and/or replacement, the noble metal or activated carbon will degrade over time and lose the ability to adsorb mercury, the reducing agent will lose the ability to adsorb the released nonmercury elements, and the lime or silica gel will lose the ability to adsorb the hydrogen chloride. The periodic maintenance and/or replacement of the noble metal, activated carbon, reducing agent, and lime or silica gel can significantly increase operating costs through down time and material replacement costs.

SUMMARY OF THE INVENTION

It is an objective of the present invention to provide a low maintenance system for accurate and reliable monitoring of speciated and/or elemental mercury concentrations in a gas.

It is a further objective to provide a method and apparatus for continuously monitoring the presence of speciated and/or elemental mercury in a gas. It is a related objective to provide real-time speciated and/or elemental mercury measurements for a gas to enable more effective control of mercury emissions and compliance with environmental regulations.

It is a further objective to provide a mercury monitoring method and apparatus that does not have a component, such as a noble metal or reducing agent, that requires periodic replacement. It is a related objective to provide a mercury monitoring method and apparatus that does not employ an amalgam or reducing agent.

The present invention addresses these and other objectives in a device for monitoring the presence of mercury in a gas containing speciated and/or elemental mercury. The device includes a gas handling system to collect a sample of the gas (e.g., provide a gas stream) for mercury monitoring and a heating means positioned to heat the gas handling system. The heating means not only increases the gas stream temperature to an operating temperature sufficient to convert the speciated mercury in the gas stream into elemental mercury but also maintains the gas stream at a sufficiently high temperature to prevent the elemental mercury from returning to the speciated form. The operating temperature is preferably no less than about 700° C. and more preferably ranges from about 900° C. to about 1000° C. The gas handling system preferably includes separate inlet and body portions for the conversion of speciated into elemental mercury, a containment portion for the passage of radiation through the gas stream, and an outlet portion for discharging the irradiated portion of the gas stream. Radiation is preferably passed through the gas stream only in the containment portion and not in the inlet and body portions of the gas handling system where conversion of speciated mercury into elemental mercury is occurring. The inlet, body and containment portions of the gas handling system are substantially resistant to speciated and elemental mercury absorption at temperatures above the gas temperature (e.g., which is preferably no less than about 900° C.) and the operating temperature to inhibit mercury collection. Accordingly, the interiors of the inlet, body and containment portions are substantially free of noble metals, such as gold and silver, and mixtures thereof and other mercury adsorbing compounds, such as activated carbon.

The containment portion of the gas handling system can be housed within the body portion. In that event, the radiation means is positioned to transmit radiation through the containment portion but not the inlet and body portions. The gas stream flows through an area between the body and containment portions (where speciated mercury is converted into elemental mercury) and then into the containment portion for mercury measurement.

For mercury detection, the device includes radiation means for transmitting radiation through the gas stream in the containment portion of the gas handling system and radiation sensitive means for receiving the unabsorbed portion of the radiation and providing a signal for use in detecting mercury in the gas stream. The radiation means includes a light source that can emit radiation having a wavelength of 2537 angstroms. The light source can be a mercury vapor lamp.

Where the gas contains mercury and radiation absorbing materials, such as nitrous oxides and sulfur oxides, the device can include a means for forming a magnetic field along the path of the radiation to provide a plurality of radiation wavelengths and/or means for selecting a radiation wavelength to determine only that amount of radiation absorbed by the elemental mercury and not by other radiation absorbing materials. The magnetic means produces a first portion of the radiation having a first wavelength at which elemental mercury and the radiation absorbing materials absorb radiation and a second portion having a second wavelength at which the radiation absorbing materials but not elemental mercury absorbs radiation. The wavelength selecting means passes at least one of these wavelengths through the containment portion for absorption by the gas stream components. The wavelength selecting means can include a rotating body having one or more openings capable of selectively passing only the selected radiation wavelength(s) into the gas stream.

Where the gas to be sampled contains both speciated and elemental mercury, the device can include a second gas handling system for mercury measurement to determine the relative concentrations of speciated and elemental mercury in the gas before conversion of speciated into elemental mercury. The second gas handling system includes a second inlet portion and second containment portion for a second gas stream (taken from the gas to be sampled) and is at a temperature less than the converter operating temperature. A beam splitting means is used to direct a first radiation portion from the radiation means through the containment portion and a second radiation portion through the second containment portion. A second radiation sensitive means receives the unabsorbed second radiation portion and provides a second signal for use in determining the amount of speciated or elemental mercury in the gas.

The above-noted device is capable of continuous monitoring of the mercury levels in the gas stream. Relative to prior art mercury detection devices, the abilities of the present invention to continuously provide real-time feedback of mercury levels in the gas stream enables more efficient control of mercury removal devices and therefore facilitates compliance with environmental regulations.

The device's conversion of speciated mercury into elemental mercury in the gas handling system and maintenance of the gas handling system at a high enough temperature to prevent speciated mercury from reforming eliminates the need for a mercury absorbing material or a reducing agent. The elimination of these materials enhances the long-term performance of the device and significantly reduces operating costs relative to prior art mercury detection devices. Unlike prior art mercury detection devices, there is no need to periodically replace such materials to maintain detector efficiency.

Unlike prior art detectors, the device does not cool the gas before mercury measurement as cooling of the gas can cause elemental mercury to condense or collect onto the walls of the device. Such mercury losses can significantly alter the mercury measurement results.

The present invention further provides a method for monitoring the presence of mercury in a gas containing speciated mercury. The method includes the steps: (i) continuously introducing a gas stream into the gas handling system during a selected time interval; (ii) maintaining, during said time interval, the inlet and containment portions of the gas handling system at an operating temperature sufficient to convert the speciated mercury into elemental mercury while the speciated mercury is in the gas stream and maintain the mercury in the elemental state; (iii) transmitting radiation through the containment portion during at least a portion of the time interval, wherein the elemental mercury absorbs a portion of the radiation; (iv) receiving the unabsorbed portion of the radiation with a radiation sensitive device; and (v) using the received radiation to generate a signal for use in monitoring the presence of mercury in the gas stream.

In the introducing step, the gas stream preferably flows through the chamber at a substantially constant rate during the time interval. The average residence time of the gas stream in the inlet portion is no less than about 2 seconds to ensure complete conversion of speciated into elemental mercury before the gas stream enters the containment portion.

To account for the presence of radiation absorbing materials other than elemental mercury in the gas stream, the transmitting step can include the substeps: (i) passing first radiation having a wavelength of 2537 angstroms through the heated gas stream, wherein the radiation absorbing material and the elemental mercury collectively absorb a first portion of the first radiation and (ii) passing second radiation having a wavelength different from 2537 angstroms through the heated gas stream, wherein the radiation absorbing material absorbs a second portion of the second radiation. The first portion is compared with the second portion to determine the amount of radiation absorbed by the elemental mercury. The first passing and second passing steps are repeated over successive time periods during the time interval to generate a plurality of signals representing alternatively the unabsorbed portions of the first radiation or second radiation received during each time period. The appropriate unabsorbed portions are used to determine the amounts of elemental mercury in the gas stream.

To control a mercury removal device, the method can include the step of comparing the signal to a predetermined value for the signal. Based thereon, an appropriate control signal is provided to the mercury removal device. For example, the signal could correspond to a specific mercury concentration in the gas stream and the predetermined value would correspond to an appropriate amount of mercury sorbent to be released into the gas for different mercury concentrations.

DETAILED DESCRIPTION OF THE PREFERRED EMBODIMENT

A mercury monitoring device is provided that can continuously determine the concentrations of speciated and/or elemental mercury in a gas. The mercury monitoring device is particularly useful in monitoring the presence of mercury in waste gases, such as from fossil fuel combustion facilities and municipal solid waste incinerators. The mercury monitoring device has a mercury measurement sensitivity below about 1 µg/m$^3$ (less than about 0.1 ppb v/v). The device has a linear response to mercury concentrations greater than about 100 µg/m$^3$.

Figure 1:
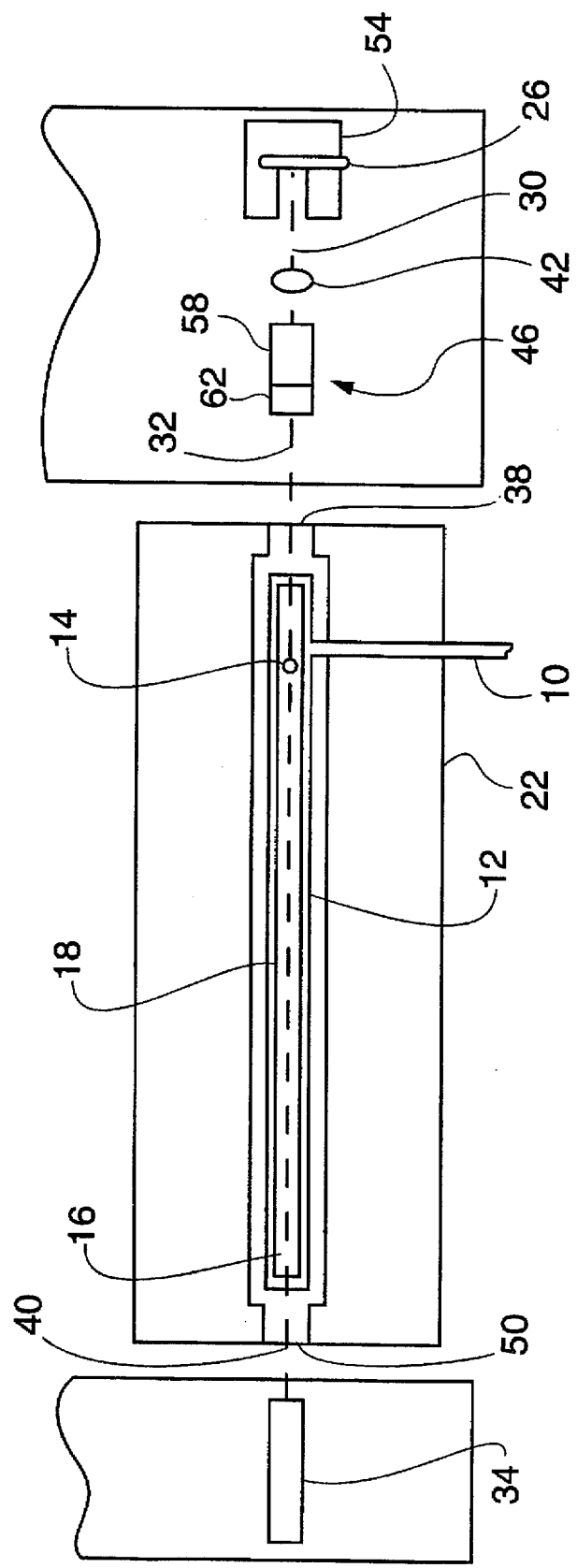
FIG. 1 is a view of the various components of a mercury monitoring device according to the present invention.

FIG. 1 illustrates the various components of a preferred embodiment of the mercury monitoring device. The device includes a gas handling system having an inlet portion 10, body portion 12, containment portion 18, and outlet portion 14 for a gas stream (which is typically a split of the gas to be monitored) and a substantially cylindrical containment portion 18 in communication therewith. The containment portion 18 is contained within the body portion 12 for improved conversion of speciated to elemental mercury before measurement. Heating means 22 surrounds the inlet, body, and containment portions and heats them to a sufficient temperature to convert speciated into elemental mercury and maintain the mercury in the elemental state. Radiation means 26, magnetic device 54, collimator 42, and means 46 for selecting the wavelength of the radiation are at one end of the containment portion 18 and cooperate to transmit radiation 32 of a selected wavelength through the containment portion 18 for mercury detection. The radiation 32 is substantially parallel to the longitudinal axis of the containment portion 18. The portion of the radiation not absorbed by the various gas stream components is received by a radiation sensitive means 34 positioned at the other end of the containment portion 18. The radiation sensitive means 34 provides a signal for use in detecting the presence of mercury in the gas stream and/or in determining the concentration of at least one of speciated mercury, elemental mercury, or both in the gas stream.

The inlet and body portions preferably have dimensions sufficient to provide a residence time for the gas stream of at least about 2 and more preferably at least about 5 seconds. The diameters and lengths of the inlet and body portions in the heating means 22 are sufficient for substantially complete conversion of the speciated mercury in the gas stream into elemental mercury. To facilitate the conversion of speciated to elemental mercury in the body portion, the body portion can include a heat transfer means to cause an increased transfer of thermal energy to the gas stream. The heat transfer means can be any substance that provides increased surface area and adequate levels of heat transfer such as glass frit, glass chips, glass wool, ceramics, metal chips or wool, or other substances that are substantially nonreactive with mercury.

The inlet and outlet portions 10, 14 are positioned at the same end of the body and containment portions to provide a desired residence time in the gas stream in the body portion 12. The inlet and body portions 10, 12 of the gas handling system preferably have a length from the inlet of the inlet portion to the inner inlet 16 sufficient to provide the residence times referred to above before mercury measurement.

The inlet, body and containment portions are substantially resistant to the absorption of speciated and elemental mercury at the gas stream temperature and the operating temperature to provide for accurate measurements. Accordingly, the inlet, body, and containment portions are substantially free of mercury absorbing materials, such as gold, silver, and other noble metals.

The heating means 22 is any suitable heating device that can heat the inlet portion 10 and the containment portion 18 to an operating temperature that is sufficient to convert the speciated mercury into elemental mercury. Preferably, the operating temperature is a temperature of no less than about 700° C. and more preferably ranging from about 900° C. to about 1000° C.

The radiation means 26 is a light source that can produce radiation having a wavelength of 2537 angstroms. As noted above, elemental mercury only absorbs radiation having this specific wavelength. Preferred light sources include a mercury vapor lamp.

Where the gas stream contains elemental mercury and other radiation absorbing materials, such as nitrous oxides and sulfur oxides, a plurality of wavelengths must be transmitted through the heated gas stream to provide the total mercury concentration. Comparison of the amounts of radiation absorbed at the various radiation wavelengths provides the amount of radiation absorbed by the elemental mercury alone and, therefore, the elemental mercury concentration in the containment portion 18. Because the strength of the signal is proportional to the amount of radiation absorbed by the various gas stream components, to calculate the total mercury concentration the strength of a first signal is determined for a first portion of radiation having a wavelength of 2537 angstroms (at which the elemental mercury and other radiation absorbing materials absorb the radiation), a strength of a second signal is determined for a second portion of radiation having a wavelength other than 2537 angstroms (at which the other radiation absorbing materials but not elemental mercury absorb radiation), and the strengths of the first and second signals are compared to determine the amount of the first portion of the radiation absorbed only by the elemental mercury. Based on this amount and the length of the containment portion, it is a straightforward mathematical computation to determine the total mercury concentration in the gas stream.

To produce the first and second radiation portions, the present invention uses means 54 for forming a magnetic field along the path of the radiation 30 and the wavelength selecting means 46. The magnetic means 54 provides a plurality of selected wavelengths in the radiation 30. As will be appreciated, through the Zeeman effect, the magnetic field will provide altered radiation 30 having three components, a middle component having the wavelength of the radiation emitted by the light source (i.e., 2537 angstroms) and plane polarized to vibrate in a direction parallel with the magnetic field (i.e., vertical) and two side components having wavelengths different from the wavelength of the middle component (which will not be absorbed by elemental mercury) and plane polarized to vibrate in a direction normal to the magnetic field (i.e, horizontal). The radiation means 26 is located at one end of the containment portion 18 adjacent to a substantially transparent containment portion surface 38 for transmission of the radiation 32 into the containment portion 18.

To pass radiation of a selected wavelength through the containment portion surface 38, the wavelength selecting means 46 is located between the radiation means 26 and containment portion 18. The wavelength selection means 46 includes a modulator 58, such as a Pockels cell and a polarizer 62. The Pockels cell rotates the linearly polarized output of the radiation means in a strong magnetic field by 90° or 0°, depending upon the bilevel input voltage to the cell. During a given time interval, the modulator 58 rotates the plane of polarization of the radiation component to be selectively passed by the polarizer 62 to a vertical orientation, and the polarizer 62 passes the component having the vertical plane of polarization. By way of example, at the lower voltage level, the Pockels cell will not rotate the plane of polarization and the polarizer 62 will pass the middle component (but not the side components) and at the higher voltage level the cell will rotate the plane of polarization by 90° and the polarizer will pass the side components (but not the middle component). The polarizer 62 will block the other component(s) which vibrate in the plane normal to the vertical plane of polarization. Thus, the middle and side components are alternately passed by the polarizer 62 through the containment portion.

A collimator 42 provides radiation 36 having a narrow range of angular orientations for the wavelength selection means 46. The collimator 42 is any suitable optical device, such as a lens, for increasing the radiation intensity.

The radiation sensitive means 34 is any suitable detector capable of providing a signal in response to the received radiation 40 that is not absorbed by the various components of the gas stream. The radiation sensitive means 34 is positioned relative to the radiation means 26 (e.g., along the longitudinal axis of the containment portion 18) so as to receive the radiation 40 that is not absorbed by the various components of the gas stream. As in the case of the radiation means 26, the radiation sensitive means 34 is located at one end of the containment portion 18 adjacent to another substantially transparent containment portion surface 50 to enable the radiation sensitive means to receive the unabsorbed radiation 40.

The positioning of the radiation means 26 and radiation sensitive means 34 at opposite ends of the containment portion 18 eliminates the need for a reducing agent in the containment portion 18. Unlike prior art mercury detectors which convert speciated mercury into elemental mercury in one vessel and cool the gas stream as it is transported to a separate vessel for mercury measurement, the mercury monitoring device of the present invention performs the conversion and measurement in the inlet portion 10 and body portion 12 and does not cool the gas stream before measurement. Because the gas stream is not cooled, the elemental mercury will not recombine with the released elements before measurement. Accordingly, it is unnecessary to remove the released elements from the gas stream through the use of a reducing agent.

Figure 14:
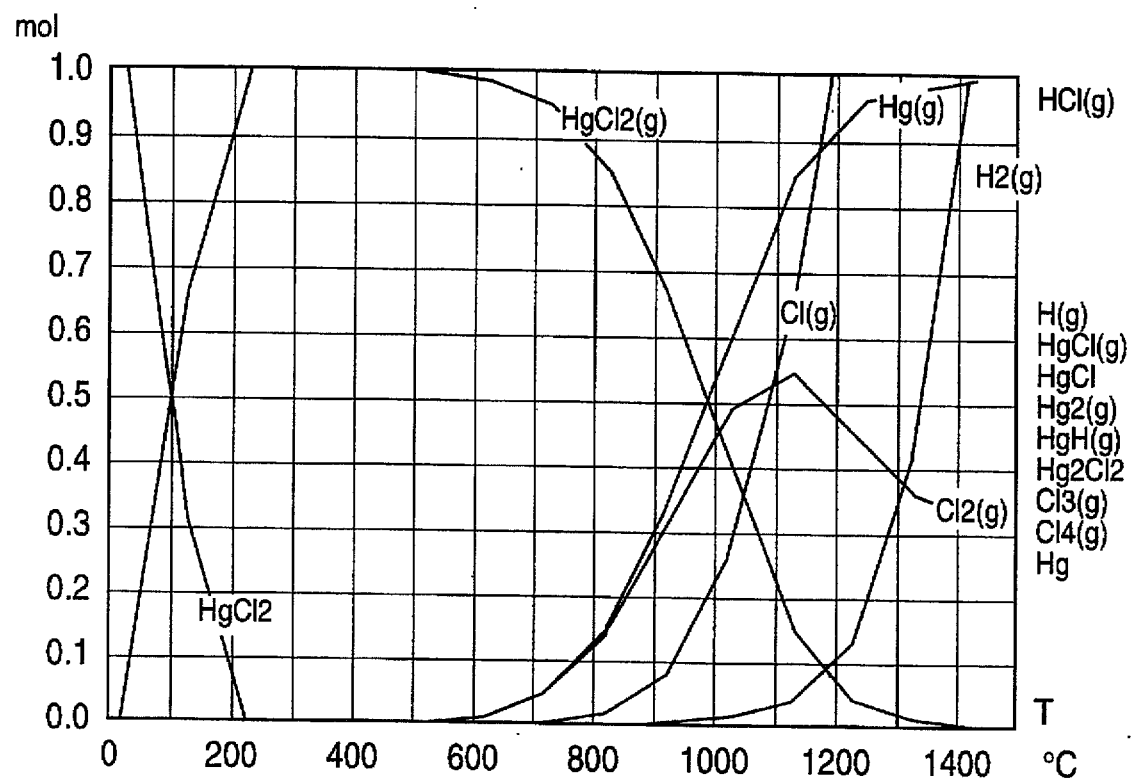
FIG. 14 is a plot of the equilibrium concentrations of mercuric chloride and elemental mercury as a function of temperature.
Figure 15:
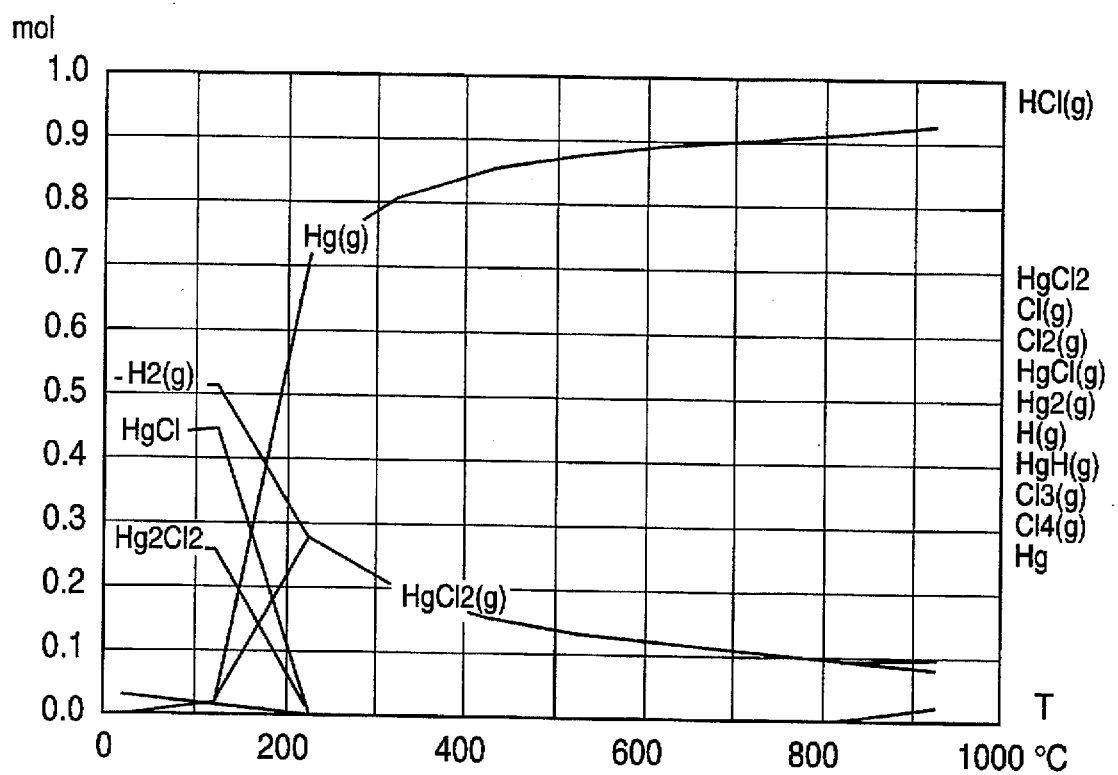
FIG. 15 is a plot of the equilibrium concentration of hydrogen chloride and mercuric chloride as a function of temperature.

By eliminating the cooling of the gas prior to elemental mercury measurement, the present invention overcomes the need for removing hydrogen chloride and other chloride-containing compounds from the gas to prevent the reverse reaction of the elemental mercury with the hydrogen chloride to form speciated mercury. Referring to FIGS. 14 and 15, the equilibrium concentrations of mercuric chloride, elemental mercury, and hydrogen chloride are shown as a function of temperature. At a temperature above about 800° C., the percentage of the total mercury in a gas that is mercuric chloride rapidly decreases relative to the amount that is elemental mercury and hydrogen chloride. FIGS. 14 and 15 may overestimate the amount of mercuric chloride because the figure fails to reflect reaction kinetics. Accordingly, the mercuric chloride concentration at the converter operating temperature can be significantly less than the concentration given in FIGS. 14 and 15. In any event, it has been discovered that maintaining the gas at a temperature of preferably no less than about 700° C., and more preferably no less than about 900° C., during mercury measurement provides a high degree of accuracy in measuring total mercury concentration.

Figure 2:
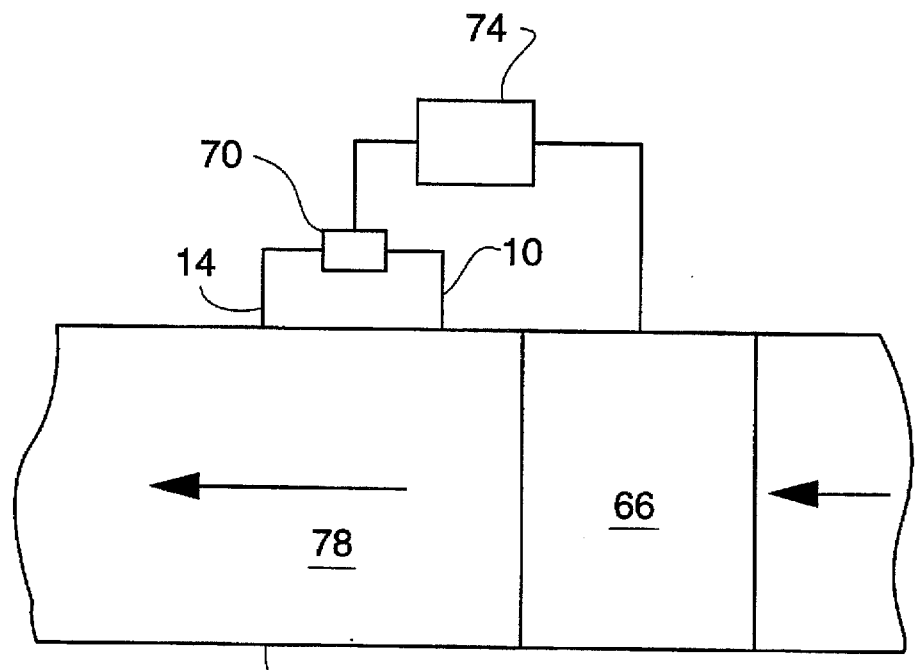
FIG. 2 is a view of the mercury monitoring device being used to monitor the mercury concentration of a gas downstream of a mercury removal device.
Figure 3:
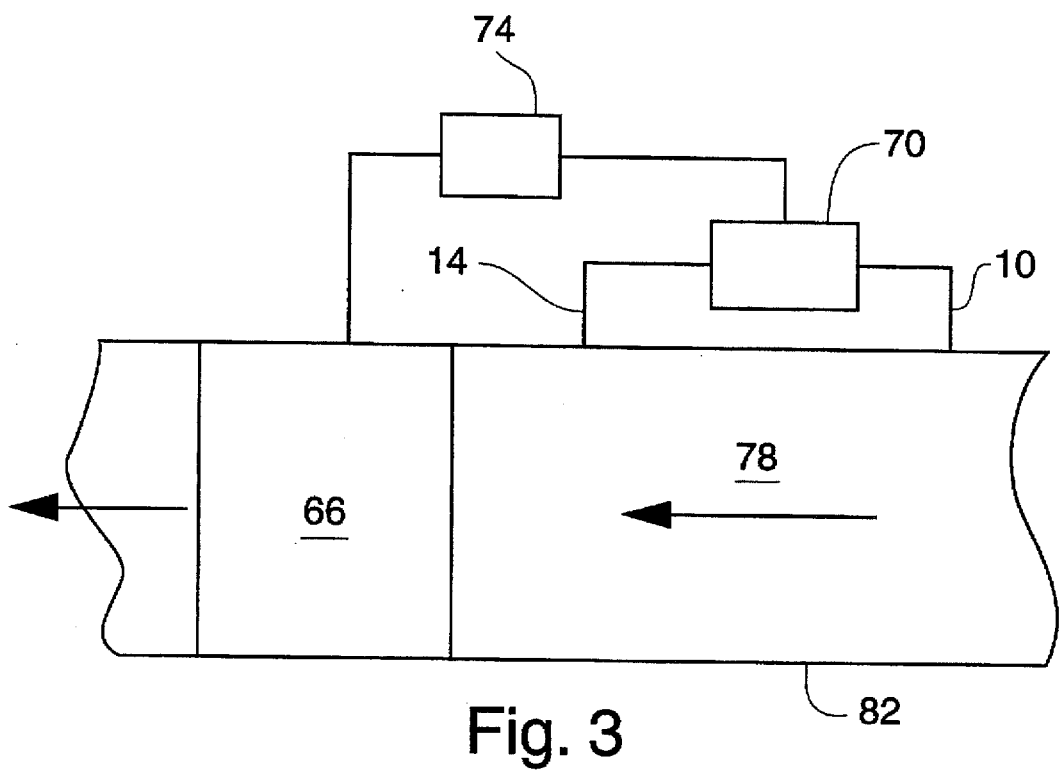
FIG. 3 is a view of the mercury monitoring device being used to monitor the mercury concentration of a gas upstream of a mercury removal device.
Figure 4:
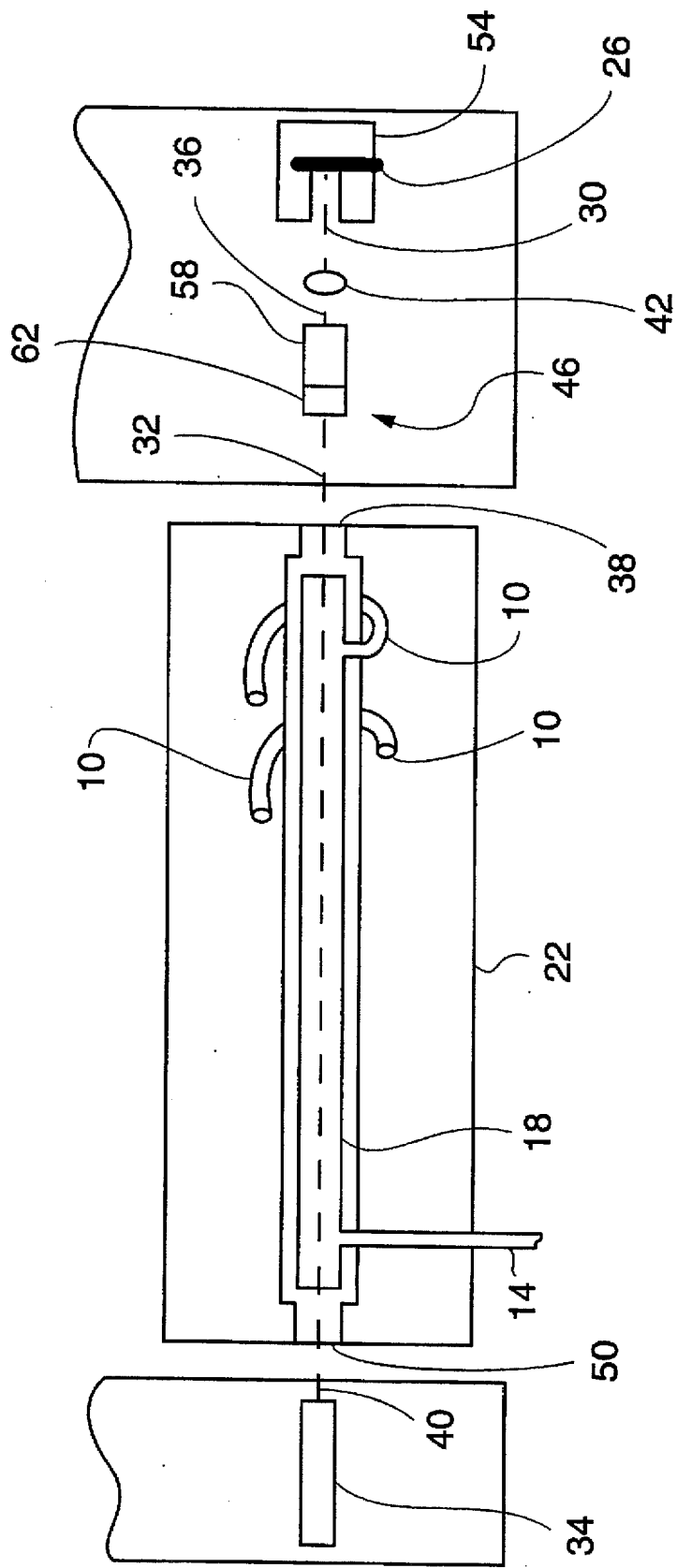
FIG. 4 is a view of another embodiment of a mercury monitoring device.

FIGS. 2 and 3 illustrate the use of the above-described mercury monitoring device to monitor the effectiveness of and/or to control the operation of a mercury removal means 66. FIG. 2 illustrates the use of a mercury monitoring device 70 with the inlet portion 10 positioned downstream of the mercury removal means 66 (which typically is a device using either a sorbent or noble metal or wet or dry scrubber for mercury removal) to monitor the effectiveness of and/or to control the operation of the mercury removal means 66. FIG. 3 illustrates the use of a mercury monitoring device 70 with the inlet portion 10 positioned upstream of the mercury removal means 66 to control the operation of the mercury removal means 66. In either case, the signal represents either the presence of elemental or speciated mercury in the gas or the concentration of at least one of elemental and speciated mercury, or both, in the gas. To control the operation of the mercury removal means 66, the signal from the mercury monitoring device is received by a computer 74 which analyzes the signal and provides a control signal to the mercury removal means 66. To analyze a signal corresponding to the concentration of elemental and/or speciated mercury, the computer 74 can compare the signal to one or more predetermined values for the signal and generate an appropriate control signal based thereon. For example in the case of a mercury removal means 66 that releases a mercury sorbent into the gas, the strength of the control signal would fluctuate depending upon the concentration of elemental and/or speciated mercury in the gas. In this manner, an amount of sorbent is released into the gas that is related to the actual concentration of elemental and/or speciated mercury in the gas, thereby reducing sorbent consumption and the operating costs of the mercury removal means 66.

The operation of the mercury monitoring device 70 of the present invention will now be described as applied to a gas containing not only speciated mercury but also other radiation absorbing materials, such as nitrous oxides and sulfur oxides, that absorb radiation over a broad spectrum of wavelengths including a wavelength of 2537 angstroms.

Referring to FIGS. 1, 2 and 3, a gas stream, which is a split of a gas 78 flowing in a conduit 82, continuously flows over a selected time interval through the gas handling system (i.e., the inlet portion 10, the body portion 12 through (i.e., the annulus between the body and containment portions) the containment portion 18, and the outlet portion 14) and is returned to the gas 78 in the conduit 82. The time interval is selected based on the desired period over which mercury detection is to be conducted. Typically, the time interval is coterminous with the duration of the gas flow through the conduit 82. Preferably, the gas stream flows into the containment portion 18 at a substantially constant rate during the selected time interval.

The inlet portion 10, body portion 12, and containment portion 18 are maintained, during the time interval, at an operating temperature sufficient to convert the speciated mercury into elemental mercury and maintain the mercury in the elemental state. The gas stream is heated to the operating temperature while passing through the inlet portion 10 and body portion 12 and maintained at the operating temperatures in the containment portion 18. The speciated mercury is converted into elemental mercury in the gas phase in the inlet portion 10 and body portion 12.

Radiation 32 of differing wavelengths is transmitted through the containment portion 18 at selected time intervals with a portion of the radiation being absorbed by the elemental mercury and a portion by other radiation absorbing materials. As noted above, to account for the other radiation absorbing materials present in the gas stream (besides elemental mercury), the transmission of the radiation 32 is done in a series of steps: (i) in a first time interval first radiation 32 having a wavelength of 2537 angstroms is passed through the heated gas stream with a first portion of the first radiation being absorbed by the radiation absorbing materials, including the elemental mercury, and (ii) in a second time interval second radiation 32 having a wavelength different from 2537 angstroms is passed through the heated gas stream with a second portion of the second radiation being absorbed by the radiation absorbing materials other than the elemental mercury. For continuous mercury monitoring, the two steps are repeated over successive time periods. Preferably, radiation 32 is transmitted through the containment portion 18 substantially continuously (i.e., switching occurs at least 300 times every second).

The unabsorbed portion 40 of the radiation is received by the radiation sensitive means 34 and the received portion of the radiation is used to generate a signal for use in monitoring the presence and/or concentration of elemental and/or speciated mercury in the gas stream and therefore the gas 78. The strength of the signal is proportional to the amount of unabsorbed radiation which is in turn proportional to the amount of radiation absorbing materials, including elemental mercury, in the gas stream. The first portion referred to above generates a first signal having a strength proportional to the amount of radiation absorbing materials, including elemental mercury, in the gas stream, and the second portion generates a second signal having a strength proportional to the amount of radiation absorbing materials excluding elemental mercury. To determine the concentration of speciated and elemental mercury, the relative strengths of the first and second signals are compared as described above.

The signal is used to generate a control signal to control the operation of the mercury removal means 66. The control signal is generated by comparing the signal to predetermined values for the signal that correspond to different speciated and/or elemental mercury concentrations.

As will be appreciated, the mercury monitoring device of the present invention can alternatively be used as a batch sampling system.

In alternative embodiments, the mercury monitoring device has other components and/or is in other configurations. The alternate embodiments are sometimes preferable in specific applications.

In another embodiment, the mercury monitoring device does not include a body portion in the gas handling system. The gas handling system has the inlet portion 10, containment portion 18, and outlet portion 14. To provide a sufficient length for the inlet portion 10 to substantially completely convert the speciated mercury in the gas stream into elemental mercury, the inlet portion 10 can be coiled, as shown, around the containment portion 18 in the heating means 22.

The inlet and outlet portions 10, 14 are positioned at opposite ends of the containment portion to provide the desired residence time of the gas stream in the containment portion 18. The containment portion 18 of the gas handling system preferably has a distance between the input and output portions sufficient to provide the residence times noted above in the containment portion 18 before mercury measurement.

The inlet portion 10 is positioned transversely to the containment portion 18 to ensure complete conversion of the speciated mercury in the gas stream to elemental mercury before the gas stream is irradiated. If the inlet and containment portions had the same longitudinal axis, the mercury measurement could be inaccurate due to the presence of speciated mercury along the path of the radiation.

In operation, the gas stream continuously flows through the inlet portion 10, the containment portion 18, and the outlet portion 14, and is returned to the gas 78 in the conduit 82. The inlet portion 10 and containment portion 18 are maintained, during the time interval, at an operating temperature sufficient to convert the speciated mercury into elemental mercury and maintain the mercury in the elemental state. The gas stream is heated to the converter operating temperature while passing through the inlet portion 10 and maintained at the operating temperature in the containment portion 18. Radiation 32 of differing wavelengths is transmitted through the containment portion 18 at selected time intervals, as described above.

Figure 5:
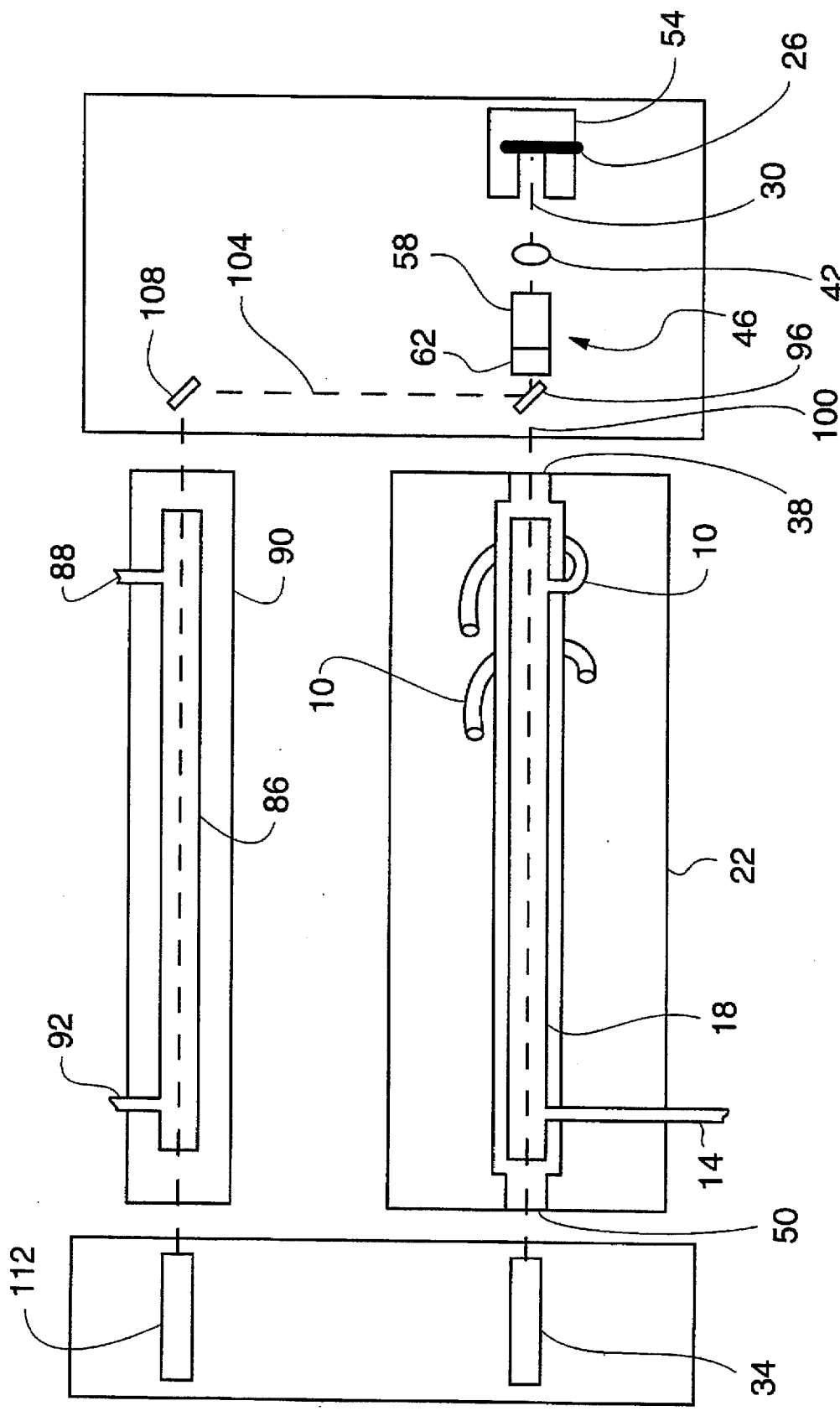
FIG. 5 is a view of another embodiment of a mercury monitoring device.

In another alternative embodiment shown in FIG. 5, the device has a second gas handling system including a second inlet portion 88 and second outlet portion 92 communicating with a second containment portion 86 for determining the concentration of speciated mercury or elemental mercury in the gas stream. The second containment portion 86 is at a temperature less than the temperature of the first containment portion 18. As desired, a second heating means 90 can be included to maintain the temperature of the second containment portion 86 at the temperature of the gas in the conduit 82. For flue gases, the second containment portion 86 is preferably maintained at a temperature ranging from about 200° C. to about 400° C. Beam splitting means 96 directs a first radiation portion 100 through the first containment portion 18 and a second radiation portion 104 through the second containment portion 86. A mirror 108 reflects the second radiation portion 104 through the second containment portion 86. A second radiation sensitive means 112 receives the unabsorbed component of the second radiation portion and provides a second signal for use in determining the amount of elemental mercury in the second gas stream. The second signal corresponds to the elemental mercury concentration in the gas 78 and can be compared with the signal for the unabsorbed first radiation portion (which represents the total mercury concentration) to determine the concentration of speciated mercury in the gas 78. This embodiment is particularly useful where the mercury removal means 66 is capable only of removing speciated or elemental mercury but not both. If other radiation absorbing materials besides elemental mercury are present, the first and second radiation portions can have their wavelengths sequentially altered as discussed above.

Figure 6:
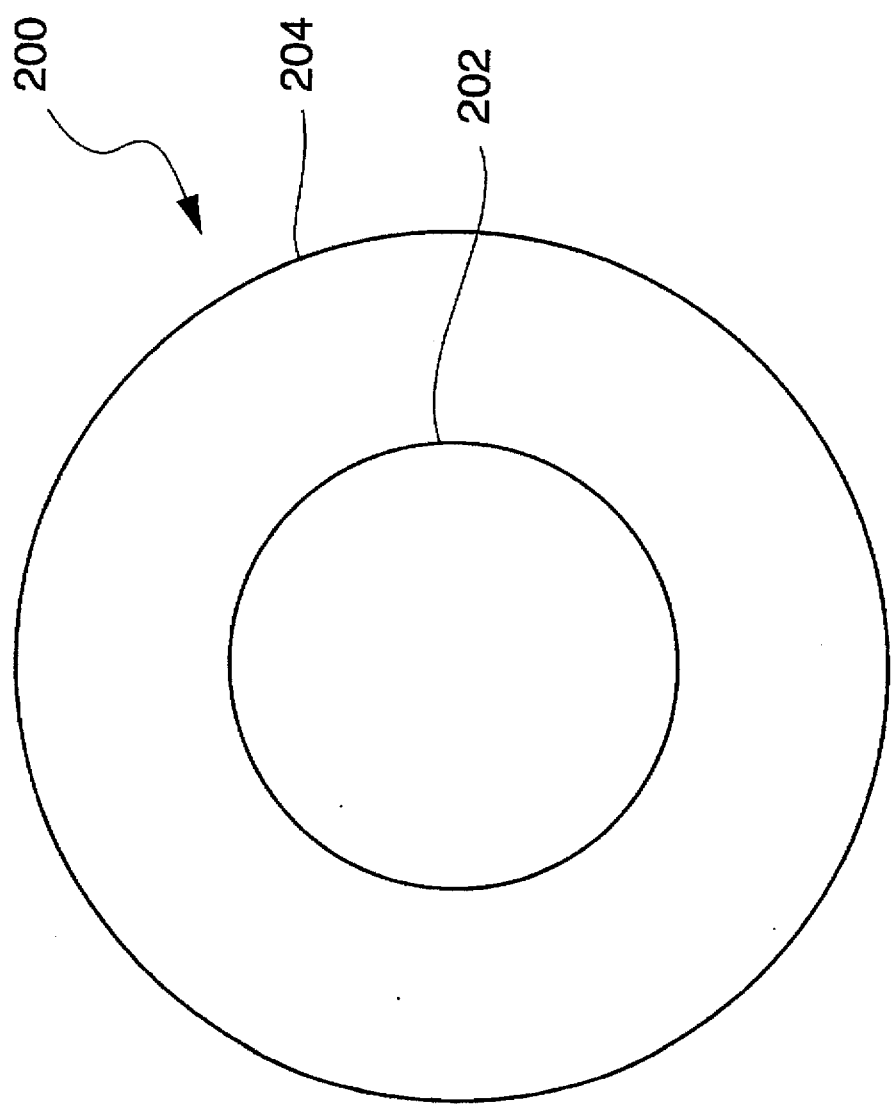
FIG. 6 is a view of a means for changing the wavelength of radiation.

In other embodiments, the modulator 58 can be a means for changing the wavelength of the radiation using the modulator 200 shown in FIG. 6. The modulator 200 is a ½-waveplate 202 (i.e., a quartz plate with a special optical coating) centered in a suitable housing 204. When the waveplate optical axis is displaced 0° from the vertical component of the magnetic field from the magnetic means 54, no polarization rotation occurs. At an angle of 45°, the polarization is rotated by 90°. Calculations predict that the behavior at any angle of rotation is given by the equation $y=a_1\cos^2 2\theta + a_2\sin^2 2\theta$, where $\theta$ is the angle between the vertical component of the magnetic field and the optical axis of the waveplate and $a_1$ and $a_2$ reflect the relative magnitudes of the absorption coefficients for the two wavelength components. It is preferred that the waveplate be rotated at a rate ranging from about 350 to about 370 rpm.

It has been discovered that the radiation output from the modulator 200 is a mixture of the middle and side components, depending upon the angle between the vertical magnetic field lines and the optical axis of the waveplate. The radiation output is therefore not as distinct as the Pockels cell referred to above, which produces radiation composed substantially entirely of either the side or middle components. An analog electronics circuit permits the elemental mercury concentration to be determined from the mixed wavelength radiation components that are output from the modulator 200 and passed through the polarizer 62.

Thus, the rotating waveplate is the exact analog of the Pockels cell, but it achieves polarization rotation through mechanical rotation rather than electronic means as with the Pockels cell.

In another embodiment, the wavelength selecting means can exclude the polarizer 62 and modulator 58. To form radiation of different wavelengths, the magnetic device 54 can be alternatively switched on and off. This embodiment has the disadvantage that it is difficult to shield the magnetic field produced by the magnetic device from interfering with the circuitry of the mercury monitoring device.

EXPERIMENT 1

A test was conducted using the dual chamber mercury detection device to determine the concentration of elemental and speciated mercury in a gas stream. Two mercury sources were used during the testing: (i) elemental mercury and (ii) mercuric chloride (e.g., $HgCl_2$). A permeation tube was used to generate elemental mercury, and a diffusion vial was fabricated to generate mercuric chloride vapor. The sources were calibrated by periodically weighing them using an analytical balance. Constant permeation rates were obtained after a suitable stabilization period. It is widely believed that elemental mercury and mercuric chloride are the two most predominant species in flue gases generated from coal combustion.

The flow rate of the test gas was approximately 800 cc/min. The concentration of the mercury sources was varied over time and ranged from 1 to 10 ppb v/v. The target for the detector was to be capable of measuring mercury concentrations down to approximately 0.1 ppb v/v. The device was able to efficiently measure the elemental and speciated mercury concentrations as they were varied over time. The speciated mercury was efficiently converted into elemental mercury before measurement.

EXPERIMENT 2

Figure 7:
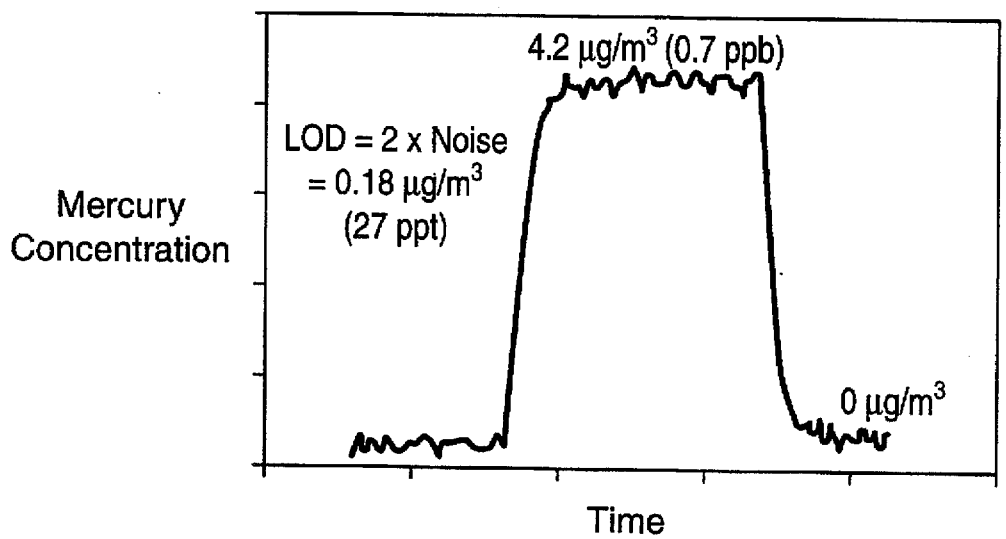
FIG. 7 shows the elemental mercury concentration measured by the mercury monitoring device versus time for a gas containing elemental mercury.

In another experiment, elemental mercury was introduced into the mercury detection device shown in FIG. 1 at a concentration of 4.2 µg/m³ (0.7 ppb v/v). FIG. 7 depicts the device's response to the mercury concentration as well as the response when no gas is in the device. Based on the peak-to-peak noise level observed, a minimum level of detection (defined as 2X noise level) of 0.2 µg/m³ (27 ppt v/v) was calculated.

Figure 8:
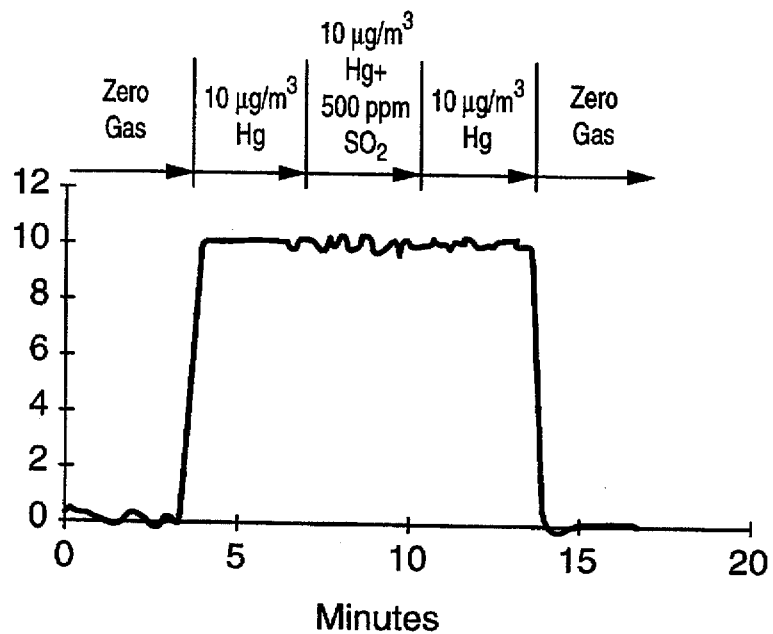
FIG. 8 is a plot of the elemental mercury concentration measured by the mercury monitoring device versus time in a gas containing elemental mercury and sulfur dioxide.

The response of the device to a gas having a mercury concentration of 10 µg/m³ and 500 ppm sulfur dioxide is depicted in FIG. 8. As can be seen from FIG. 8, the device eliminates the effects of interfering gases such as sulfur dioxide.

Figure 9:
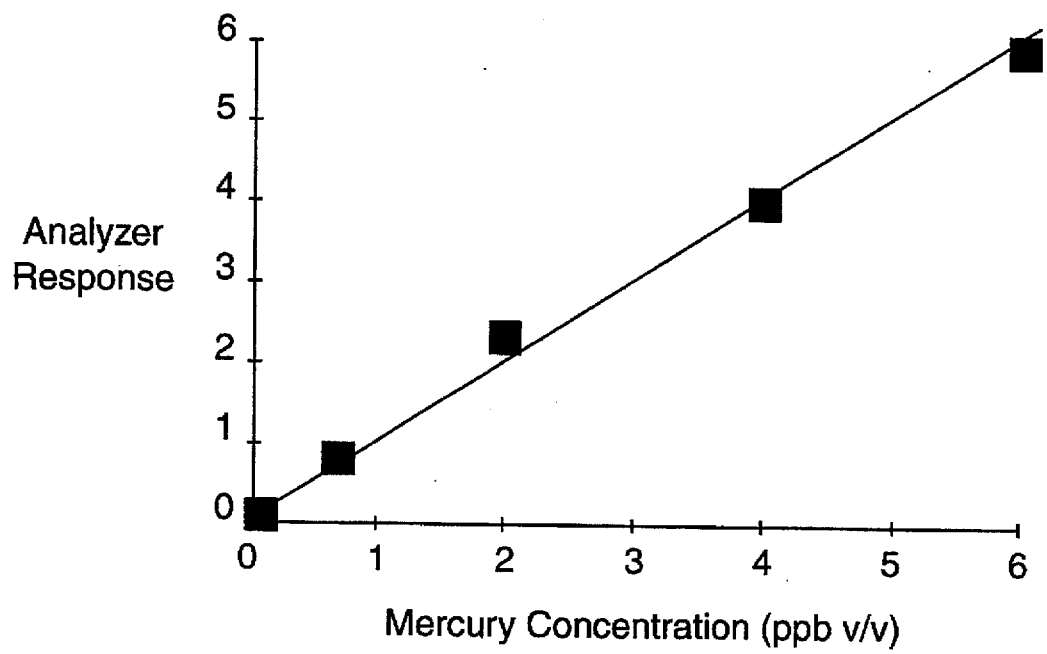
FIG. 9 is a plot of the elemental mercury concentration measured by the mercury monitoring device in a gas in which the elemental mercury concentration was varied over time.

The mercury concentration in the gas was varied over a concentration range of 0–6 ppb (v/v). The range is expected to cover most concentrations expected in coal-fired and municipal solid waste generated flue gases. A dilution probe was used on the analyzer where high concentrations of mercury were expected, such as when monitoring uncontrolled emissions ahead of an APCD. FIG. 9 shows the linear response of the analyzer over the concentration range.

EXPERIMENT 3

A mercury monitoring device different from the device shown in FIG. 1 was employed to determine the ability of the converter to convert speciated mercury into elemental mercury. The device had a separate converter and mercury measurement device. The converter thermally cracked the chemical bonds in two surrogate speciated mercury compounds—mercuric chloride and dimethyl mercury. The gas sample was then cooled to a temperature of about 200° C. and contacted with a fixed bed of tin to remove chlorine. The cooled gas sample was input into the mercury measurement device which irradiated the sample to measure elemental mercury concentration. A bypass valve was employed to permit the gas sample to bypass the converter and be input directly into the mercury measurement device.

Figure 10:
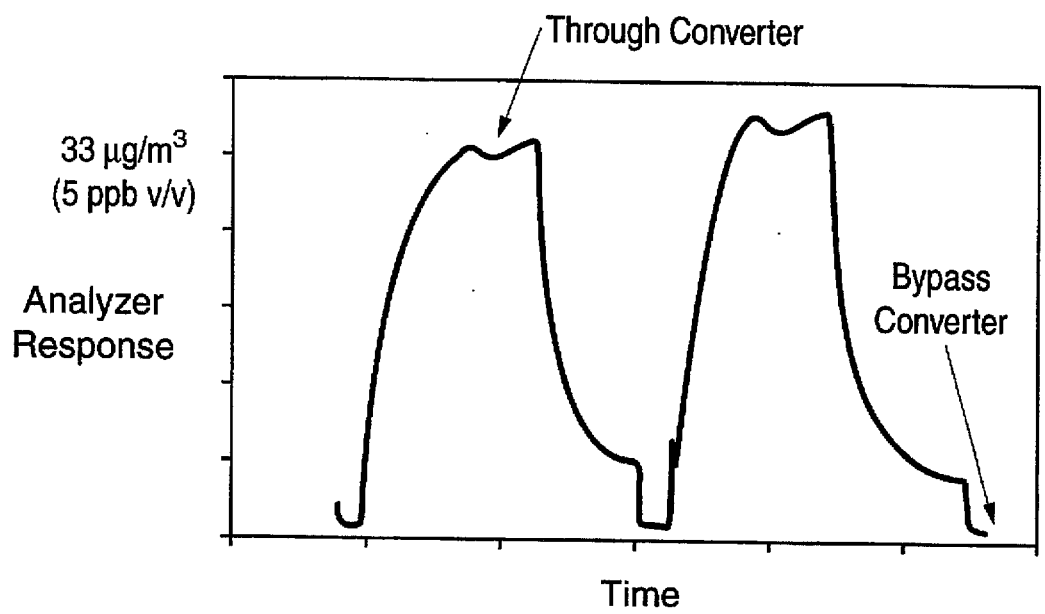
FIGS. 10 and 11 show the elemental mercury concentration measured by the mercury monitoring device versus time in a gas containing two surrogate speciated mercury compounds that were converted prior to mercury measurements.
Figure 11:
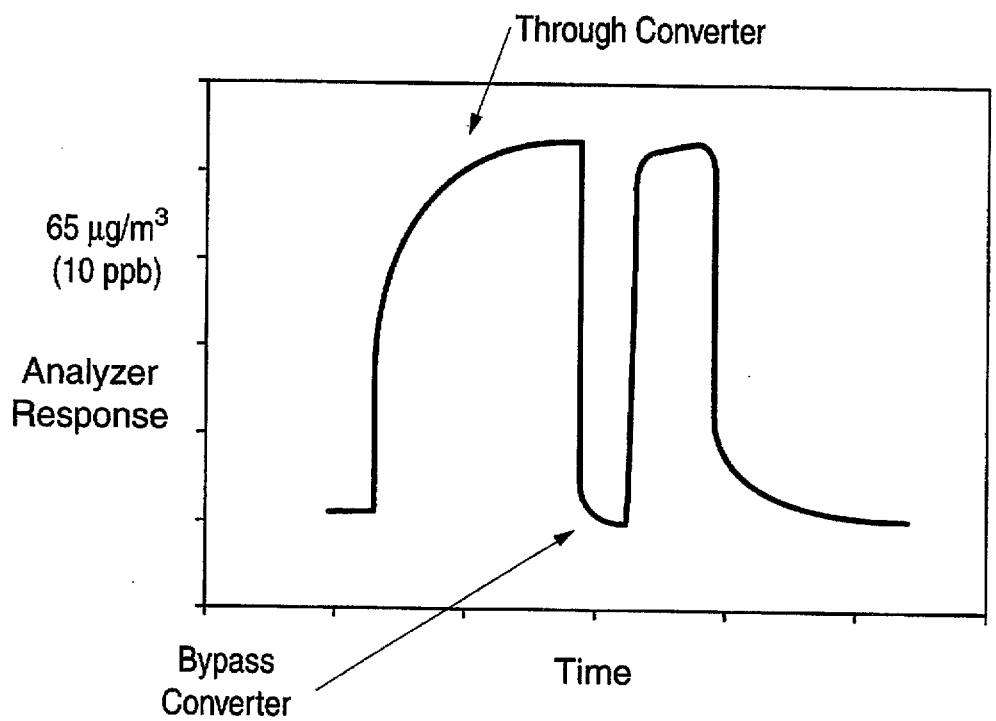

FIGS. 10 and 11 show the response of the device when the gas sample was alternately diverted through the converter to the mercury measurement device (i.e., which is reflected by the rises in mercury concentration) and when the sample bypassed the converter and was input directly into the device (i.e., which is reflected by the drops in mercury concentration). The bypass valve was alternately actuated and deactuated in a sequence to alternately pass the sample through the converter or around the converter. The sequence was repeated for a number of cycles to establish the fact that substantially all of the speciated mercury was being converted to elemental mercury.

EXPERIMENT 4

Figure 12:
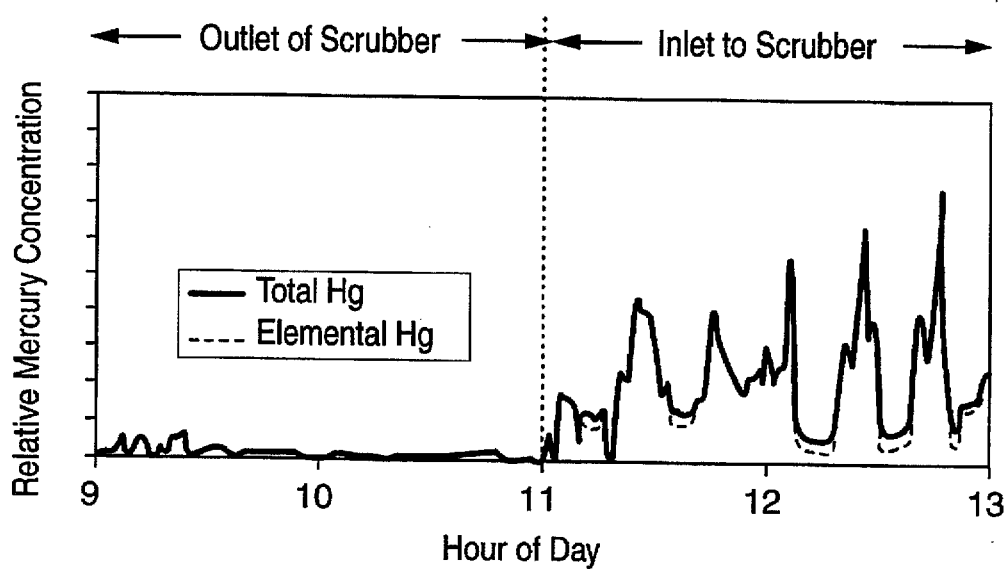
FIG. 12 is a plot of the total mercury concentration continuously measured by the mercury monitoring device in a waste gas entering and leaving a scrubber over a 4-hour period of time.
Figure 13:
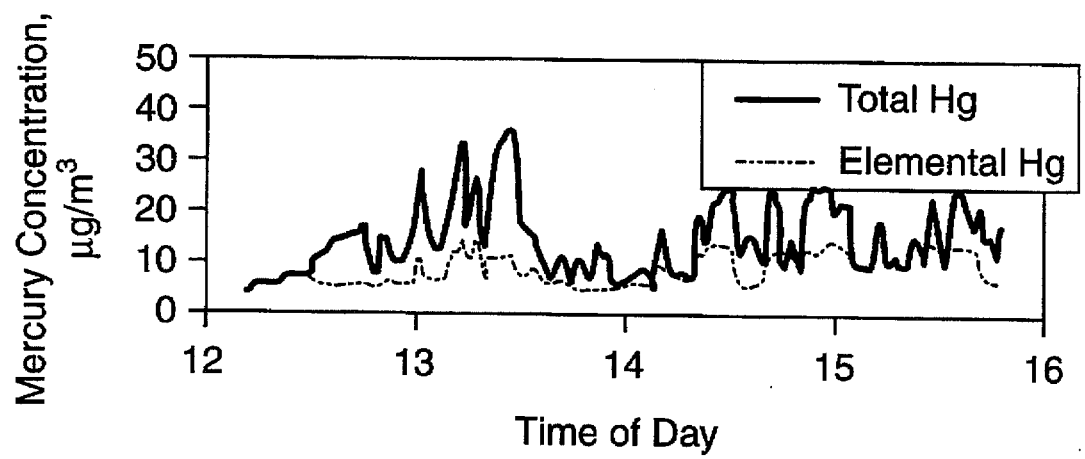
FIG. 13 is a plot of total and elemental mercury concentration measured by the mercury monitoring device versus time for the waste gas output from the scrubber over a 4-hour period of time.

The device shown in FIG. 5 was tested at a pilot-scale thermal treatment facility. The treatment system was intended to reduce the volumes of hazardous waste being containerized and stored at the facility. The system included a plasma hearth chamber, a secondary combustor, an acid gas scrubber, a baghouse, and a bank of HEPA filters. At the time of testing, the facility was evaluating a unique mercury removal system and the analyzer was used to measure concentrations of mercury entering and exiting the system. FIG. 12 shows relative concentrations of total and elemental mercury entering and leaving the mercury scrubber over a 4-hour period of time. FIG. 13 shows concentrations of total and elemental mercury leaving the scrubber over a 4-hour period. The "spikes" in concentration correlate to the input of wastes to the thermal treatment unit. The difference in mercury readings between the total and elemental measurements is the concentration of speciated mercury (i.e., the concentration of chemically combined mercury).

The above-described series of tests shows that the device responds rapidly to changes in mercury concentration, and that the device tracks the mercury emissions as a function of the input waste gas.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A device for monitoring the presence of mercury in a gas stream, comprising:

a gas handling system having a containment portion, an inlet portion, and an outlet portion for passage of a gas stream therethrough, said gas stream including speciated mercury and the interior of said inlet portion and containment portion being substantially resistant to the absorption of speciated and elemental mercury at or above the temperature of said gas stream;

heating means for heating said inlet portion and containment portion to at least an operating temperature, said operating temperature being sufficient to convert said speciated mercury into elemental mercury;

radiation means for transmitting radiation having a first wavelength through said gas stream in said containment portion, wherein a portion of said radiation is absorbed by said elemental mercury;

a device for forming a magnetic field along the path of said radiation to produce a first portion of said radiation having said first wavelength and a second portion having a second wavelength; and radiation sensitive means for receiving said unabsorbed portion of said radiation and for providing a signal for use in detecting the presence of mercury in said gas stream.

2. The device as claimed in claim 1, wherein:

said speciated mercury includes at least one of the following mercury-containing compounds: mercuric chloride, methyl marcuric chloride, marcuric oxide, dimethyl mercury and mixtures thereof.

3. The device as claimed in claim 1, wherein:

said interior of said inlet portion and containment portion are substantially free of a noble metal.

4. The device as claimed in claim 1, wherein:

said inlet portion is positioned traverse to said containment portion.

5. The device as claimed in claim 1, wherein:

said inlet portion and containment portion are substantially free of a solid or liquid reducing agent.

6. The device as claimed in claim 1, wherein:

said inlet portion has a length sufficient for substantially complete conversion of said speciated mercury in said gas stream into elemental mercury.

7. The device as claimed in claim 1, wherein:

said inlet portion is substantially free of radiation.

8. The device as claimed in claim 1, wherein:

said inlet and outlet portions each communicate with a conduit containing a gas containing speciated mercury and said gas stream is a portion of said gas.

9. The device as claimed in claim 1, wherein:

said operating temperature is no less than about 700° C.

10. The device as claimed in claim 9, wherein:

said operating temperature ranges from about 900° to about 1000° C.

11. The device as claimed in claim 9, wherein:

said radiation means includes at least one of the following: a mercury vapor lamp and other lamps capable of producing radiation having a wavelength of 2537 angstroms.

12. The device as claimed in claim 1, wherein:

said radiation has a wavelength of 2537 angstroms.

13. The device as claimed in claim 1, wherein said radiation has a plurality of wavelengths and further comprising:

means for selecting a wavelength located between said radiation means and said containment portion.

14. The device as claimed in claim 1, wherein said radiation has a plurality of wavelengths and further comprising:

means for selecting a wavelength located between said radiation means and said containment portion, said means for selecting including a rotating body having a waveplate for passing radiation of a selected wavelength into said containment portion.

15. The device as claimed in claim 1, wherein:

said inlet portion and said outlet portion each communicate with a conduit containing a gas containing speciated and elemental mercury and said gas stream is a portion of said gas; and further comprising:

mercury removal means for removing at least one of said speciated and elemental mercury from said gas, wherein said signal is used to control said mercury removal means.

16. The device as claimed in claim 1 wherein:

said inlet portion and said outlet portion each communicate with a conduit containing a gas containing speciated and elemental mercury; and further comprising:

a second gas handling system including a second containment portion, at a temperature less than said operating temperature, a second inlet portion and a second outlet portion in said conduit for continuous passage of a second gas stream therethrough, said second gas stream being a portion of said gas;

beam splitting means for directing a first radiation portion from said radiation means through said containment portion and a second radiation portion through said second containment portion, wherein a portion of said second radiation portion is absorbed by elemental mercury in said second gas stream; and second radiation sensitive means for receiving an unabsorbed component of said second radiation portion and for providing a second signal for use in determining the amount of elemental mercury in said second gas stream.

17. The device as claimed in claim 1, wherein:

said containment portion is contained within said input portion.

18. A method for monitoring the presence of mercury in a gas stream containing speciated mercury, comprising:

continuously introducing said gas stream into a gas handling system during a selected time interval;

maintaining, during said time interval, an input portion and a containment portion of said gas handling system at an operating temperature sufficient to convert said speciated mercury to elemental mercury while said speciated mercury is in said gas stream;

passing radiation through a magnetic field to form altered radiation;

transmitting altered radiation through said containment portion during at least a portion of said time interval, wherein said elemental mercury absorbs a portion of said altered radiation;

receiving said unabsorbed portion of said altered radiation with a radiation sensitive device; and using said received radiation to generate a signal for use in monitoring the presence of mercury in said gas stream.

19. The method as claimed in claim 18, wherein said introducing step comprises:

flowing said gas stream through said containment portion at a substantially constant rate during said time interval.

20. The method as claimed in claim 18, wherein:

in said introducing step, said gas stream has an average residence time in said containment portion that is no less than about 2 seconds.

21. The method as claimed in claim 18, wherein said gas stream includes a radiation absorbing material that is substantially free of mercury and said transmitting step comprises:

passing first radiation having a wavelength of 2537 angstroms through said heated gas stream, wherein said radiation absorbing material and said elemental mercury collectively absorb a first portion of said first radiation; and passing second radiation having a wavelength different from 2537 angstroms through said heated gas stream, wherein said radiation absorbing material absorbs a second portion of said second radiation; and further comprising:

comparing said first portion with said second portion to determine the amount of radiation absorbed by said elemental mercury.

22. The method as claimed in claim 18, wherein said gas stream includes a radiation absorbing material that is substantially free of mercury and said transmitting step comprises:

first passing first radiation having a wavelength of 2537 angstroms through said heated gas stream, wherein said radiation absorbing material and said elemental mercury collectively absorb a first portion of said first radiation; and second passing second radiation having a wavelength different from 2537 angstroms through said heated gas stream, wherein said radiation absorbing material absorbs a second portion of said second radiation, wherein said first passing and second passing steps are repeated over successive time periods during said time interval to generate a plurality of said signals.

23. The method as claimed in claim 18, wherein:

said gas stream is a portion of a gas and said signal corresponds to an amount of at least one of speciated mercury, elemental mercury, and mixtures thereof in said stream; and further comprising:

comparing said signal to a predetermined value for said signal and based thereon providing a control signal; and using said control signal to control a mercury removal device contacting said gas.

24. A method for monitoring the presence of mercury in a gas stream containing speciated mercury and another radiation absorbing material, comprising:

continuously introducing said gas stream into an inlet portion of a gas handling system during a selected time interval, said gas handling system being substantially free of a noble metal and a solid or liquid reducing agent;

maintaining, during said time interval, said gas handling system at an operating temperature no less than about 900° C. to convert said speciated mercury to elemental mercury in said inlet portion while said speciated mercury is in said gas stream;

passing first radiation having a wavelength of 2537 angstroms through said heated gas stream, wherein said radiation absorbing material and said elemental mercury collectively absorb a first portion of said first radiation;

passing second radiation having a wavelength different from 2537 Angstroms through said heated gas stream, wherein said radiation absorbing material absorbs a second portion of said second radiation; and comparing said first and second portions to determine a signal corresponding to the presence of mercury in said gas stream.

25. A device for monitoring the presence of mercury in a gas stream, comprising:

a gas handling system having a containment portion, an inlet portion, and an outlet portion for passage of a gas stream therethrough, said gas stream including speciated mercury and the interior of said inlet portion and containment portion being substantially resistant to the absorption of speciated and elemental mercury at or above the temperature of said gas stream;

heating means for heating said inlet portion and containment portion to at least an operating temperature, said operating temperature being sufficient to convert said speciated mercury into elemental mercury;

radiation means for transmitting radiation through said gas stream in said containment portion, wherein a portion of said radiation is absorbed by said elemental mercury; and radiation sensitive means for receiving said unabsorbed portion of said radiation and for providing a signal for use in detecting the presence of mercury in said gas stream, wherein said inlet portion and containment portion are substantially free of a solid or liquid reducing agent.

26. The device as claimed in claim 25, wherein:
said speciated mercury includes at least one of the following mercury-containing compounds: mercuric chloride, methyl mercuric chloride, mercuric oxide, dimethyl mercury and mixtures thereof.

27. The device as claimed in claim 25, wherein:
said interior of said inlet portion and containment portion are substantially free of a noble metal.

28. The device as claimed in claim 25, wherein:
said inlet portion is positioned traverse to said containment portion.

29. The device as claimed in claim 25, wherein:
said inlet portion has a length sufficient for substantially complete conversion of said speciated mercury in said gas stream into elemental mercury.

30. The device as claimed in claim 25, wherein:
said inlet portion is substantially free of radiation.

31. The device as claimed in claim 25, wherein:
said inlet and outlet portions each communicate with a conduit containing a gas containing speciated mercury and said gas stream is a portion of said gas.

32. The device as claimed in claim 25, wherein:
said operating temperature is no less than about 700° C.

33. The device as claimed in claim 32, wherein:
said operating temperature ranges from about 900° to about 1000° C.

34. The device as claimed in claim 32, wherein:
said radiation means includes at least one of the following: a mercury vapor lamp and other lamps capable of producing radiation having a wavelength of 2537 angstroms.

35. The device as claimed in claim 25, wherein said radiation has a wavelength of 2537 angstroms.

36. The device as claimed in claim 25, wherein said radiation has a plurality of wavelengths and further comprising:
means for selecting a wavelength located between said radiation means and said containment portion.

37. The device as claimed in claim 25, wherein said radiation has a first wavelength and further comprising:
a device for forming a magnetic field along the path of said radiation to produce a first portion of said radiation having a first wavelength and a second portion having a second wavelength.

38. The device as claimed in claim 25, wherein said radiation has a plurality of wavelengths and further comprising:

means for selecting a wavelength located between said radiation means and said containment portion, said means for selecting including a rotating body having a waveplate for passing radiation of a selected wavelength into said containment portion.

39. The device as claimed in claim 25, wherein:
said inlet portion and said outlet portion each communicate with a conduit containing a gas containing speciated and elemental mercury and said gas stream is a portion of said gas; and further comprising:
mercury removal means for removing at least one of said speciated and elemental mercury from said gas, wherein said signal is used to control said mercury removal means.

40. The device as claimed in claim 25, wherein:
said inlet portion and said outlet portion each communicate with a conduit containing a gas containing speciated and elemental mercury; and further comprising:
a second gas handling system including a second containment portion, at a temperature less than said operating temperature, a second inlet portion and a second outlet portion in said conduit for continuous passage of a second gas stream therethrough, said second gas stream being a portion of said gas;
beam splitting means for directing a first radiation portion from said radiation means through said containment portion and a second radiation portion through said second containment portion, wherein a portion of said second radiation portion is absorbed by elemental mercury in said second gas stream; and
second radiation sensitive means for receiving an unabsorbed component of said second radiation portion and for providing a second signal for use in determining the amount of elemental mercury in said second gas stream.

41. The device as claimed in claim 25, wherein:
said containment portion is contained within said input portion.

42. A device for monitoring the presence of mercury in a gas stream, comprising:

a gas handling system having a containment portion, an inlet portion, and an outlet portion for passage of a gas stream therethrough, said gas stream including speciated mercury and the interior of said inlet portion and containment portion being substantially resistant to the absorption of speciated and elemental mercury at or above the temperature of said gas stream;

heating means for heating said inlet portion and containment portion to at least an operating temperature, said operating temperature being sufficient to convert said speciated mercury into elemental mercury;

radiation means for transmitting radiation through said gas stream in said containment portion, wherein a portion of said radiation is absorbed by said elemental mercury; and radiation sensitive means for receiving said unabsorbed portion of said radiation and for providing a signal for use in detecting the presence of mercury in said gas stream, wherein said containment portion is contained within said input portion.

43. A device for monitoring the presence of mercury in a gas stream, comprising:

a gas handling system having a containment portion, an inlet portion, and an outlet portion for passage of a gas stream therethrough, said gas stream including speciated mercury;

heating means for heating said inlet portion and containment portion to at least an operating temperature, said operating temperature being sufficient to convert said speciated mercury into elemental mercury;

radiation means for generating radiation of a plurality of wavelengths;

means for polarizing the radiation to form polarized radiation, the polarizing means being located between said radiation means and said containment portion, wherein a portion of said polarized radiation is absorbed by said elemental mercury; and radiation sensitive means for receiving said unabsorbed portion of said radiation and for providing a signal for use in detecting the presence of mercury in said gas stream.

44. The device of claim 43, wherein the polarizing means includes a rotating body having a waveplate for passing altered radiation of a selected wavelength through the gas stream in the containment portion.

45. The device of claim 43, wherein the polarizing means is at least one of a polarizer and a waveplate.

46. The device of claim 43, further comprising means for rotating the radiation.

47. A device for monitoring the presence of mercury in a gas containing both speciated and elemental mercury, comprising:

a first gas handling system having a first containment portion, a first inlet portion, and a first outlet portion for passage of a gas stream therethrough, the first gas stream being at least a portion of the gas;

heating means for heating said first inlet portion and first containment portion to at least an operating temperature, said operating temperature being sufficient to convert said speciated mercury into elemental mercury;

radiation means for transmitting radiation through said gas stream in said first containment portion, wherein a portion of said radiation is absorbed by said elemental mercury;

first radiation-sensitive means for receiving said unabsorbed portion of said radiation and for providing a signal corresponding to the presence of speciated mercury in said gas, wherein said first inlet portion and said outlet portion each communicate with a conduit containing the gas containing both speciated and elemental mercury;

a second gas handling system including a second containment portion, at a temperature less than said operating temperature, a second inlet portion and a second outlet portion in communication with said conduit for continuous passage of a second gas stream therethrough, said second gas stream being at least a portion of said gas;

beam splitting means for directing a first radiation portion from said radiation means through said first containment portion and a second radiation portion through said second containment portion, wherein a portion of said second radiation portion is absorbed by elemental mercury in said second gas stream; and second radiation sensitive means for receiving an unabsorbed component of said second radiation portion and for providing a second signal corresponding to the presence of elemental mercury in said gas.

* * * * *